United States Patent [19]

Kimura

[11] 4,343,768
[45] Aug. 10, 1982

[54] GAS DETECTOR
[75] Inventor: Mitsuteru Kimura, Tagajyo, Japan
[73] Assignee: Ricoh Co., Ltd., Tokyo, Japan
[21] Appl. No.: 171,387
[22] Filed: Jul. 23, 1980
[30] Foreign Application Priority Data Jul. 25, 1979 [JP] Japan ................................. 54-93638

[51] Int. Cl.³ ........................................... G01N 27/06
[52] U.S. Cl. .................................. 422/97; 23/232 E; 338/34; 422/98
[58] Field of Search ........................... 422/95, 97, 98; 23/232 E; 73/23; 324/71 R; 338/34

[56] References Cited

U.S. PATENT DOCUMENTS

| | | | |
|---|---|---|---|
| 3,479,257 | 11/1969 | Shaver | 422/95 X |
| 3,901,067 | 8/1975 | Boardman, Jr. | 422/98 X |
| 4,039,941 | 8/1977 | Morrison | 422/98 X |
| 4,259,292 | 3/1981 | Ichinose | 422/98 |

*Primary Examiner*—Ronald E. Serwin
*Attorney, Agent, or Firm*—Burgess, Ryan and Wayne

[57] ABSTRACT

A gas detector of the type using an electric heater in which a substrate consists of an upper film of electrically insulating substance having a resistance to heat and a lower film of substance different from the substance of the upper film, a recess is formed below or under the upper film by removing part of the lower film, and a film of electrically conductive substance is deposited over the bridge of the upper film across the recess in the lower film, thereby providing a heating element characterized in that said heating element consists of a film of a substance having catalytic effects in the presence of a gas to be detected deposited on said electrically conductive substance or a material responsive to a gas to be detected, or consists of said electrically conductive substance having catalytic effects in the presence of a gas to be detected or a substance containing said substance having catalytic effects in the presence of a gas to be detected or a substance responsive to a gas to be detected, and said heating element is exposed to a gas to be detected.

17 Claims, 25 Drawing Figures

GAS DETECTOR

BACKGROUND OF THE INVENTION

The present invention relates to an electric heater of a gas detector of the type in which electrical resistance is varied when the electric heater contacts and burns a flammable gas or when the electric heater contacts and reacts with a gas such as carbon monoxide or chlorine, whereby the presence of a gas is detected in terms of the variation in electrical resistance.

In general, the contact-burn type gas detectors and semiconductor type gas detectors use an electric heater for heating a gas detecting element. Obviously, it is preferable that the eletric heater consumes less power and has a low thermal time constant. To this end, the electric heater must be designed and constructed very compactly in size so that its thermal capacity can be decreased to a minimum degree.

In these gas detectors, bridge circuits are almost exclusively used in order to measure the variation in electrical resistance across a gas detecting element. However, the changes of environmental conditions such as temperature change cause the unbalance of a bridge circuit, thus causing malfunctions. In order to overcome this problem, there has been proposed a method for inserting into a bridge circuit a compensating resistor having the same characteristics as a detecting element. In the gas detectors of the type described above, the characteristics of electric heaters must be uniform, but it is extremely difficult to design and construct the electric heaters with the uniform characteristics. In addition, the manufacturing costs are very expensive. Furthermore, it is also very difficult to design and construct in such a way that two electric heaters are disposed in relatively closely spaced apart relationship.

In the gas detectors of the type described above, a heating element consists of a film of an electrically conductive element deposited over a bridge of a silicon dioxide film as will be described in detail below. When the bridge and the conductive film over it are the same in width, the bridge cannot be heated uniformly over its entire length because heat is more easily dissipated at the ends than the center of the bridge. As a result, the center of the bridge is overheated and subsequently broken.

When the electric heater of the type described above is used as a temperature detector which detects the temperature in terms of the variations in electrical resistance in response to temperature changes of a substance used as the electric heater, the sensitivity of the temperature sensor becomes very low because such local heating as described above will not cause appreciable variations in electrical resistance of the electric heater.

The electric heater of the type described must have a small thermal time constant, a higher degree of response and a higher degree of sensitivity as well.

SUMMARY OF THE INVENTION

The present invention was made to overcome the above and other problems encountered in the prior art electric heaters used in gas detectors.

One of the objects of the present invention is to provide a gas detector which employs an electric heater which consumes less power, can be integrated and can heat locally on a substrate.

Briefly stated, the present invention provides a gas detector of the type using an electric heater in which a substrate consists of an upper film of an electrically insulating substance also having resistance to heat and a lower film of a substance different from that of the upper film, a recess is formed below or under the upper film by removing part of the lower film, and a film of an electrically conductive substance is deposited over the bridge of the upper film across the recess in the lower film, thereby providing a heating element, characterized in that the heating element consists of a film of a substance having catalytic effects in the presence of a gas to be detected deposited on said electrically conductive substance or a material responsive to a gas to be detected, or consists of said electrically conductive substance having catalytic effects in the presence of a gas to be detected or a substance containing said substance having catalytic effects in the presence of a gas to be detected or a substance responsive to a gas to be detected, and said heating element is exposed to a gas to be detected.

BRIEF DESCRIPTION OF THE DRAWINGS

Same reference numerals are used to designate similar parts throughout the figures.

DESCRIPTION OF THE PREFERRED EMBODIMENTS

First Embodiment

Figure 1:
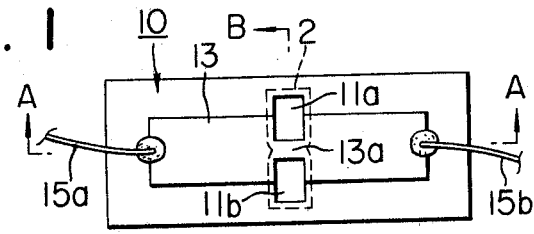
FIG. 1 is a top view of a first embodiment of the present invention.
Figure 2A:
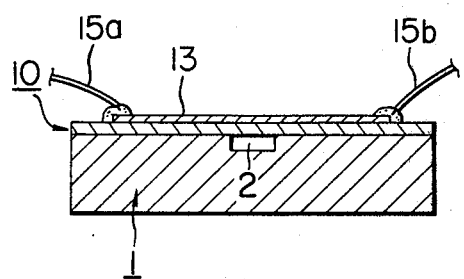
FIG. 2A is a sectional view taken along the line A—A of FIG. 1.

A first embodiment of the present invention is shown in top view in FIG. 1, in cross section taken along the line A—A of FIG. 1 in FIG. 2A, and also in cross section taken along the line B—B of FIG. 1 in FIG. 2. A silicon dioxide film 10, which is thermally grown over the major surface of a silicon wafer 1, has a high resistance to heat, a high degree of electrical insulation and a high degree of mechanical strength. An etchant which can attack the silicon wafer 1, is ineffective against the silicon dioxide film 10. A recess 2 is formed in the Si wafer 1 while forming slits 10a and 10b, in the silicon dioxide film 10 in a manner to be described below.

The Si wafer 1 is placed in a vapor atmosphere and oxidized at 1100° C. for a few hours, whereby the silicon oxide film 10 is grown to the thickness of the order of 1.0 micrometer. Thereafter, the silicon dioxide film 10 is etched by the conventional photo-etching technology. For instance, the silicon dioxide film 10 is first etched with an ammonium fluoride series etchant and then the Si wafer 1 is etched with a silver glycol etchant whose etching rate is substantially uniform in all directions independently of the direction of crystal growth, whereby two grooves are formed to a suitable depth. Thereafter, an etchant which attacks silicon anisotropically but is substantially ineffective against SiO2, is used to positively attack the side faces of the grooves, whereby the recess 2 is formed by undercutting the below the silicon dioxide film 10 and thereby connecting between the grooves. Therefore a SiO2 bridge 10a is left.

Next is formed a conductive film 13 by the sputtering process. The conductive film 13 consists of Pt or a mixture of a substance with a relatively high temperature coefficient of resistance with Pt or Pd which causes the catalytic reactions in the presence of a gas to be detected. Thereafter, leads 15a and 15b are attached to the conductive film 13. When the current flows through the leads 15a and 15b, the bridge 13a is heated. When a flammable gas exists around the bridge 13a, the former is burned so that the resistance of the bridge 13a changes. It follows, therefore, that the presence of the inflammable gas can be detected in terms of the change in electrical resistance. Alternatively, when the conductive film 13 consists of a substance such as $SnO_2$ which reacts or responds to carbon dioxide or chlorine; that is, which changes its electrical resistance when such a toxic gas attaches to or is absorbed by the conductive film 13, the toxic gas can be detected.

Second Embodiment

Figure 2B:
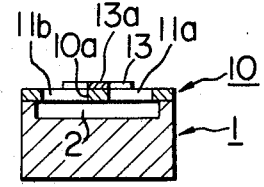
FIG. 2B is a sectional view taken along the line B—B of FIG. 1.
Figure 3:
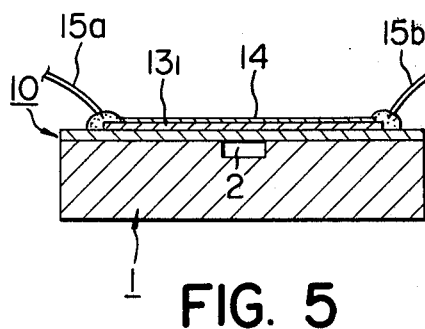
FIG. 3 is a longitudinal sectional view of a second embodiment.

In FIG. 3 is shown in cross section a second embodiment of the present invention which is substantially similar in construction to the first embodiment shown in FIGS. 1, 2A and 2B except that a conductive film $13_1$ consists of a substance such as SiC which has a high temperature coefficient of resistance and a gas responsive film 14 of $SiO_2$ or the like or a catalytic film of Pt, Pd or the like is formed over the conductive layer $13_1$. Since the bridge or heating area 13a of the conductive film $13_1$ is formed independently of the catalytic or gas responsive film 14 and has a temperature coefficient of resistance higher than that of the film 14, the sensitivity can be remarkably improved.

Third Embodiment

Figure 4:
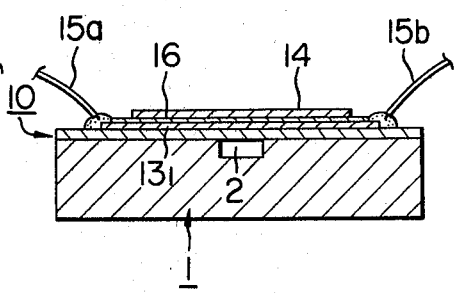
FIG. 4 is a longitudinal sectional view of a third embodiment.

In FIG. 4 is shown a third embodiment of the present invention which is substantially similar in construction to the second embodiment just described above with reference to FIG. 3 except that an insulating film 16 is interposed between the conductive film $13_1$ and the catalytic or gas responsive film 14. It is preferable to directly attach the catalytic or gas responsive film 14 to the bridge or heating area 13a. However, when the bridge 13a tends to react with gases at high temperatures or when the resistance of the bridge 13a changes when directly attached to the catalytic or gas responsive film 14, the insulating film 16 serves to seal the bridge 13a or the conductive film $13_1$ or to electrically isolate the bridge 13a or the conductive film $13_1$ from the catalytic or gas responsive film 14, whereby the above-described problems can be solved.

Fourth Embodiment

Figure 5:
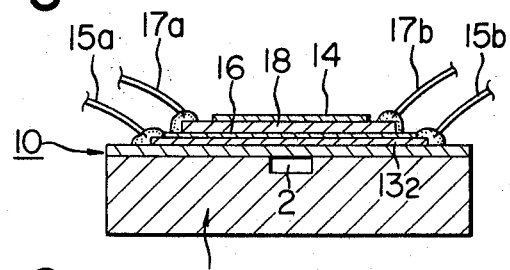
FIG. 5 is a longitudinal sectional view of a fourth embodiment.

In FIG. 5 is shown a fourth embodiment of the present invention which is substantially similar in construction to the third embodiment just described above with reference to FIG. 4 except the structual features to be described below. Formed over the insulating film 16 is a SiC film from 0.2 to 0.5 micrometers in thickness. The SiC film 18 has a temperature coefficient of resistance higher than that of the conductive film $13_2$ in an operating temperature range of, for instance, from 200° to 500° C. The catalytic or gas responsive film 14 is formed over the SiC film 18 and lead wires 17a and 17b are attached to the SiC film 18.

Fifth Embodiment

Figure 6:
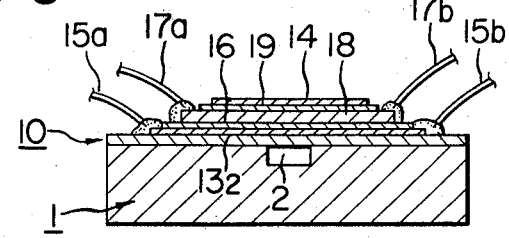
FIG. 6 is a longitudinal sectional view of a fifth embodiment.

A fifth embodiment shown in FIG. 6 is substantially similar in construction to the fourth embodiment shown in FIG. 5 except that an insulating film 19 is interposed between the SiC film 18 and the catalytic or gas responsive film 14.

In both the fourth and fifth embodiments, it is not needed to use a substance having a high temperature coefficient of resistance when the bridge or heating area (the conductive film $13_2$) is formed. In other words, the conductive film $13_2$ can be made of a substance with a relatively low temperature coefficient of resistance.

Sixth Embodiment

Figure 7:
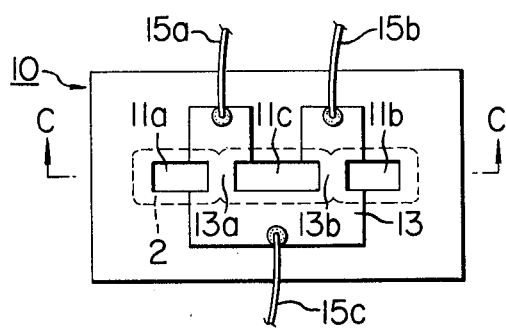
FIG. 7 is a top view of a sixth embodiment of the present invention.
Figure 8:
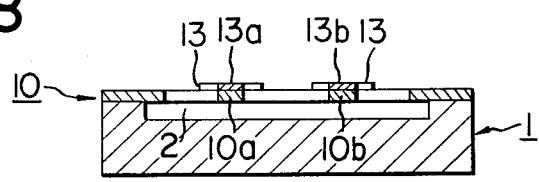
FIG. 8 is a sectional view taken along the line C—C of FIG. 7.

A sixth embodiment of the present invention is shown in FIGS. 7 and 8. The $SiO_2$ film 10 is formed with three slits 11a, 11b and 11c separated from each other by bridges 10a and 10b over which are formed heating areas 13a and 13b, respectively, of the conductive film 13.

Seventh Embodiment

Figure 9:
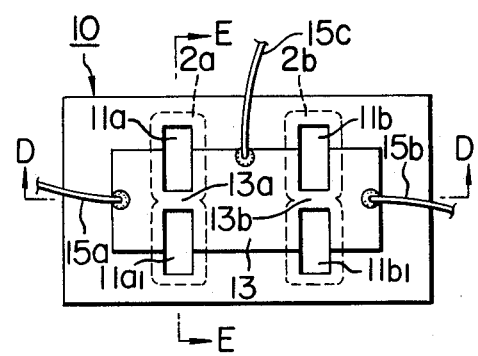
FIG. 9 is a top view of a seventh embodiment of the present invention.
Figure 10:
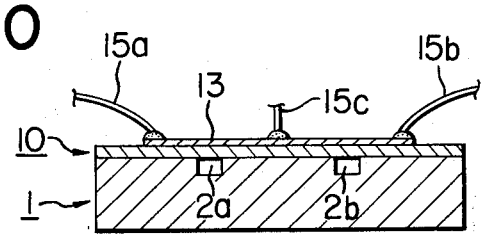
FIG. 10 is a sectional view taken along the line D—D of FIG. 9.
Figure 11:
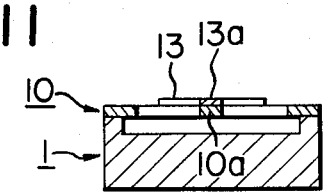
FIG. 11 is a sectional view taken along the line E—E of FIG. 9.

In a seventh embodiment shown in FIGS. 9, 10 and 11, two slit pairs 11a and $11a_1$ and 11b and $11b_2$ are formed in the silicon dioxide film 10. The slits 11a and $11a_1$ and the slits 11b and $11b_1$ are separated from each other by $SiO_2$ bridges 10a and 10b (not shown), and heating areas 13a and 13b are formed over these bridges.

Both the sixth and seventh embodiments have a common feature that there can be provided two heating areas 13a and 13b which are closely spaced apart from each other and have substantially similar characteristics.

Eighth Embodiment

Figure 12:
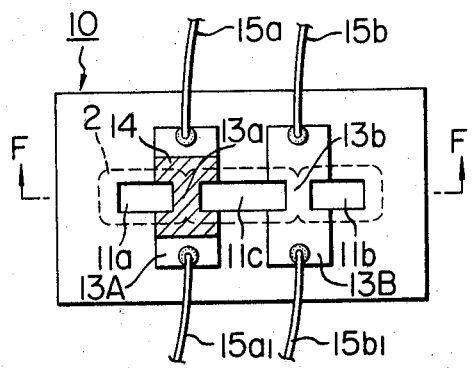
FIG. 12 is a top view of an eighth embodiment of the present invention.
Figure 13:
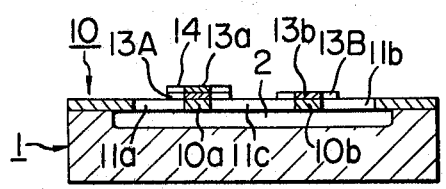
FIG. 13 is a longitudinal sectional view taken along the line F—F of FIG. 12.

An eighth embodiment shown in FIGS. 12 and 13 is also similar in construction to the sixth embodiment except that the heating areas or elements 13a and 13b are electrically isolated from each other. Therefore, separate conductive films 13A and 13B are formed and connected to lead wires 15a and 15$a_1$ and 15b and 15$b_1$. In addition, either of the bridges or heating areas 13a or 13b (13a in this embodiment) is formed with a film 14 which is not active to a gas to be detected.

Ninth Embodiment

Figure 14:
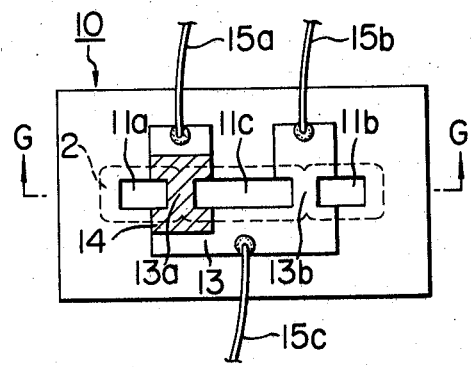
FIG. 14 is a top view of a ninth embodiment of the present invention.
Figure 15:
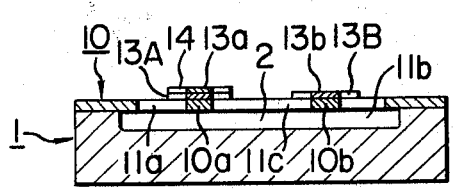
FIG. 15 is a longitudinal sectional view taken along the line G—G of FIG. 14.

A ninth embodiment shown in FIGS. 14 and 15 is also similar in construction to the sixth embodiment shown in FIGS. 7 and 8 except that a film which is not active to a gas to be detected is formed over either of the bridges or heating areas 13a or 13b (13a in this embodiment).

Both the eighth and ninth embodiments are adapted to be inserted into bridge circuits.

Tenth Embodiment

Figure 16:
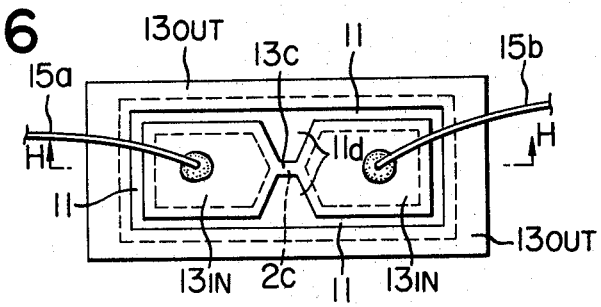
FIG. 16 is a top view of a tenth embodiment of the present invention.
Figure 17:
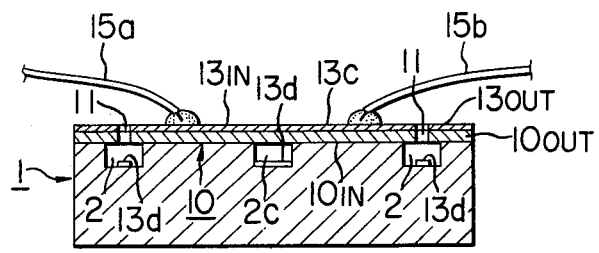
FIG. 17 is a longitudinal sectional view thereof taken along the line H—H of FIG. 16.

In a tenth embodiment shown in FIGS. 16 and 17, a rectangular slit or groove 11 is formed in the SiO$_2$ film 10, and at the centers of the long sides of this rectangular slit or groove 11 are recessed inwardly in the form of a trapezoid 11d, whereby the SiO$_2$ region 10$_{in}$ surrounded by the rectangular slit or groove 11 is notched at 11d and divided into symmetrical portions connected by a narrow bridge over a recess 2c. Therefore when the conductive film is formed by the sputtering process or the like, the inner and outer conductive films 13$_{in}$ and 13$_{out}$ are separated by the rectangular slit or groove 11. In this case, as indicated at 13d, the conductive substance is also deposited on the bottom of the recess 2 through the slit or groove 11, but their presence will not have any adverse effect on the operations of the gas detector.

The tenth embodiment is advantageous in that no masking process is needed when the conductive films 13 are formed.

11th Embodiment

Figure 18:
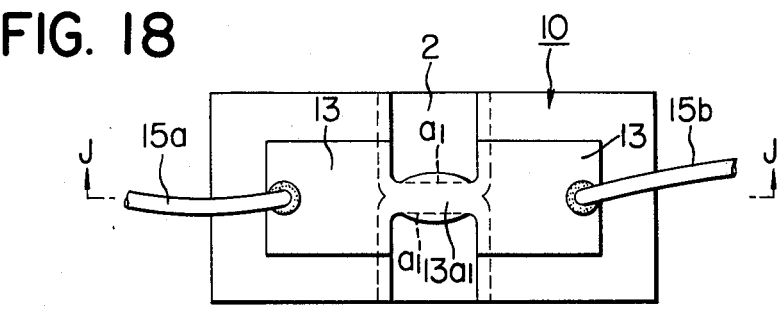
FIG. 18 is a top view of an 11th embodiment of the present invention.
Figure 19:
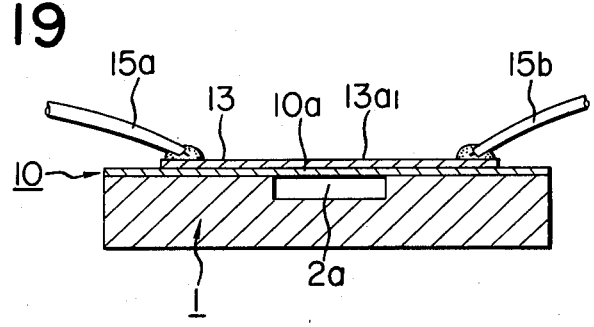
FIG. 19 is a longitudinal sectional view thereof taken along the line J—J of FIG. 18.

In an 11th embodiment shown in FIGS. 18 and 19, a bridge 13$a_1$ is so formed that its resistance is gradually increased from the center toward the ends. As a result, the bridge 13$a_1$ has a uniform distribution.

12th Embodiment

Figure 20:
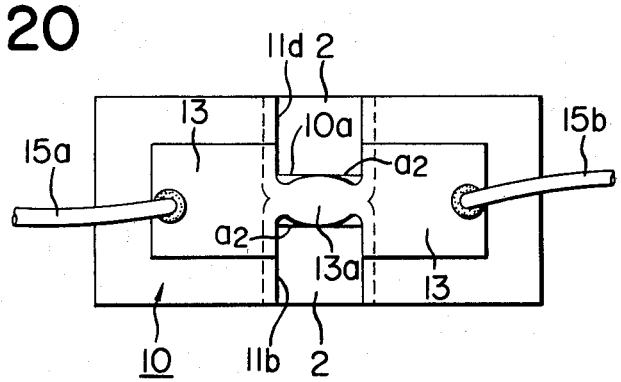
FIG. 20 is a top view of a 12th embodiment of the present invention.

In the 11th embodiment, the width of the bridge 10a of the SiO$_2$ film 10 is same with the narrowest width of the bridge 13a of the conductive film 13 as indicated by the dotted lines $a_1$ in FIG. 18, but in a 12th embodiment shown in FIG. 20, the width of the SiO$_2$ bridge 10a is made equal to the widest width of the conductive layer bridge 13a as indicated by the solid lines $a_2$.

13th Embodiment

Figure 21:
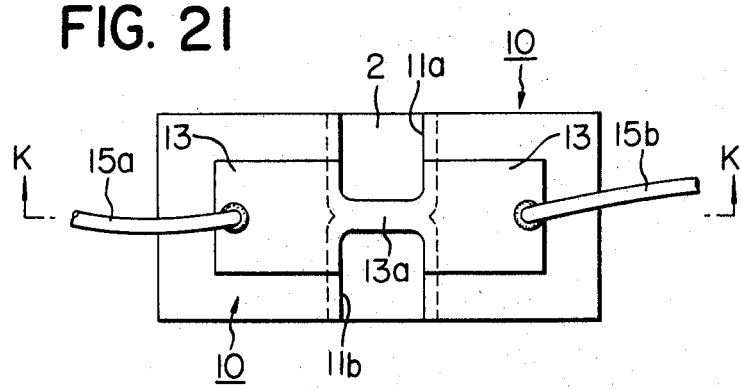
FIG. 21 is a top view of a 13th embodiment of the present invention.
Figure 22:
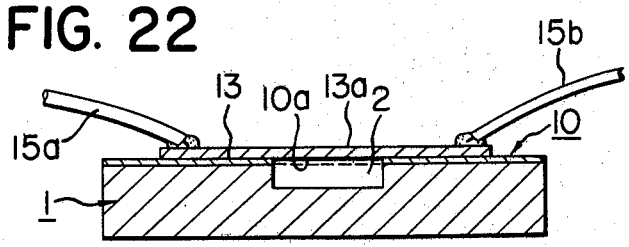
FIG. 22 is a longitudinal sectional view thereof taken along the line K—K of FIG. 21.

A 13th embodiment shown in FIGS. 21 and 22 is substantially similar in construction to the 11th embodiment shown in FIGS. 18 and 19 except that a part of SiO$_2$ film 10a under the conductive film bridge 13a is eliminated.

14th Embodiment

Figure 23:
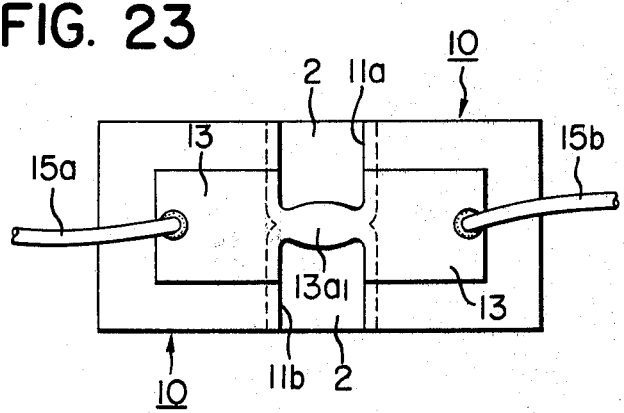
FIG. 23 is a top view of a 14th embodiment of the present invention.

A 14th embodiment shown in FIG. 23 is substantially similar in construction to the 12th embodiment shown in FIG. 20 except that as with the case of the 13th embodiment, the SiO$_2$ bridge 10a under the conductive film bridge 13a is eliminated.

Both the 13th and 14th embodiments are advantageous in that both response and sensitivity can be improved because the conductive film bridges 13a have a low thermal time constant.

Figure 24:
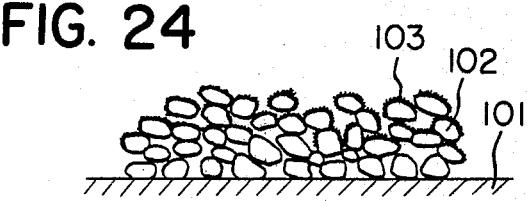
FIG. 24 is a view used for the explanation of a process for forming porous films in accordance with the present invention.

Process for forming porous films, FIG. 24

The conductive films 13 and the catalytic or gas responsive films 14 formed thereover are both porous. Such films can be formed as follows.

Referring to FIG. 24, the so-called gold black film 102 is formed by evaporating gold (Au) in a hard vacuum of the order of a few torrs over the surface of a glass substrate 101. The gold black film 102 consists of extremely fine particles and is porous. Thereafter, platinum (Pt) is deposited to the thickness of the order of 100 Å over the gold black film 102 in an argon (Ar) gas atmosphere of 100 mm torr by the sputtering or vacuum evaporation process. Then platinum penetrates deep into the porous surface of the gold black film 102 and is deposited over the surfaces of pores. Thus, a porous platinum film 103 is provided. Like platinum black, the porous Pt film 103 has an extremely large surface area and is, therefore, very advantageous when used in the contact-burn type gas detecting elements.

Platinum black is manufactured by various methods such as the reduction of aqueous solution of platinum salts or the like, the electroplating from chloroplatinic acid, a method for applying chloroplatinic acid solution, drying in hydrogen gas and heating at 500° C., thereby reducing platinum black, and so on. These methods are of the wet process, and in addition, some methods need heating processes at high temperatures.

According to the present invention, however, porous films can be formed by dry and low-temperature processes as described above. In addition, porous alloy films can be formed by the suitable selection of sputtering materials. For instance, with an 80:20 source of platinum and palladium by weight percent, a gold black film is covered with a Pt-Pd film so that a porous Pt-Pd film is provided.

The above described process utilizes scattering of gas particles so that the latter can be deposited over the surfaces of extremely small pores.

It is to be understood that the heating elements in accordance with the present invention are not limited in use to the gas detectors and may be used in various fields. For instance, they may be applied to the thermal flow meters of the type utilizing the variations in resistance in response to temperature variations. In addition, they may be also used in Pirani gauges.

What is claimed is:

1. A gas detector of the type using an electric heater in which a substrate comprises an upper film and a lower film, said upper film being made of an electrically insulating substance having a resistance to heat while said lower film is made of a substance different from that of said upper film; a recess is formed under said upper film by removing part of said lower film; and an electrically conductive substance is disposed on said upper film at a portion immediately above said recess, thereby providing a heating element, characterized in that the heating element consists of a film of a substance having catalytic effects in the presence of a gas to be detected, or a material responsive to a gas to be detected, deposited on said electrically conductive substance, or consists of said electrically conductive substance having catalytic effects in the presence of a gas to be detected or a substance containing said substance having catalytic effects in the presence of a gas to be detected or a substance responsive to a gas to be detected, and said heating element is exposed to a gas to be detected.

2. A gas detector as set forth in claim 1 further characterized in that a catalytic or gas responsive film is formed over said electrically conductive substance film directly or through an electrically insulating film.

3. A gas detector as set forth in claim 1 further characterized in that an electrically insulating film is formed over said electrically conductive substance film, a film of a substance having a high temperature coefficient of resistance in an operating temperature range is formed over said electrically insulating film, and a catalytic or gas responsive film is formed over said second mentioned film directly or through an electrically insulating film.

4. A gas detector as set forth in claim 1 further characterized in that two bridges across said recess of said upper film are formed in relatively closely spaced apart relationship, said electrically conductive substance is deposited over said upper film in such a way that said two bridges become heating elements, and one of the electrodes is connected in common to said heating elements.

5. A gas detector as set forth in claim 1 further characterized in that two bridges of said upper film are formed across said recess in relatively closely spaced apart relationship, and said electrically conductive substance is deposited over said upper film in such a way that said bridges become heating elements.

6. A gas detector as set forth in claim 5 further characterized in that one of said heating elements is coated with a substance which will not respond to a gas to be detected.

7. A gas detector as set forth in claim 1 further characterized in that said slit is provided in the form of a closed rectangular loop, and one pair of the parallel sides of said closed rectangular slit are projected inwardly in such a way that a pair of symmetrical projections are formed and separated from each other by a suitable distance.

8. A gas detector as set forth in claim 1 further characterized in that said bridge of said electrically conductive film has such an electrical resistance distribution that the resistance is gradually increased from the center to the ends of said bridge.

9. A gas detector as set forth in claim 1 further characterized in that the bridge of said lower film immediately under the bridge of said electrically conductive film is removed.

10. A gas detector of the type using an electric heater in which a substrate comprises an upper film and a lower film, said upper film being made of an electrically insulating substance having a resistance to heat while said lower film being made of a substance different from that of said upper film; a recess is formed under said upper film by removing part of said lower film; and an electrically conductive substance is disposed on said upper film at a portion immediately above said recess, thereby providing a heating element, characterized in that said heating element consists of said electrically conductive substance combined with a substance having catalytic effects in the presence of a gas to be detected or with a substance responsive to a gas to be detected, and said heating element is exposed to a gas to be detected.

11. A gas detector comprising
(a) a substrate,
(b) at least one recess formed in said substrate,
(c) an electrically insulating film which is formed to bridge across said recess at the portion at which is formed a heater for detecting a gas, and
(d) an electrically conductive film which is formed over said electrically insulating film so as to provide said heater and electrodes.

12. A gas detector as set forth in claim 11 wherein a catalytic layer is formed over said heater of said electrically conductive film.

13. A gas detector as set forth in claim 12 wherein an electrically insulating film is interposed between said catalytic film and said heater.

14. A gas detector as set forth in claim 12 or 13 wherein said catalytic layer comprises a metal oxide containing at least Pt and/or Pd.

15. A gas detector as set forth in claim 11 wherein said electrically conductive film and/or said electrically insulating film is so formed as to attain a uniform temperature distribution.

16. A gas detector as set forth in claim 15 wherein said electrically insulating film has a curved configuration.

17. A gas detector, comprising:
(a) a substrate,
(b) at least one recess formed in said substrate,
(c) an electrically insulating film which is formed to bridge said recess at the portion at which is formed a heater for detecting a gas,
(d) an electrically conductive film which is formed on said electrically insulating film so as to provide said heater and electrodes, and
(e) a catalytic film which is formed over said heater of said electrically conductive film.

* * * * *